United States Patent
Ho

(10) Patent No.: US 11,917,774 B2
(45) Date of Patent: Feb. 27, 2024

(54) QUICKLY-FIXABLE ELECTRONIC DEVICE

(71) Applicant: OXTI CORPORATION, New Taipei (TW)

(72) Inventor: Chih-Feng Ho, New Taipei (TW)

(73) Assignee: OXTI CORPORATION, New Taipei (TW)

(*) Notice: Subject to any disclaimer, the term of this patent is extended or adjusted under 35 U.S.C. 154(b) by 456 days.

(21) Appl. No.: 17/206,088

(22) Filed: Mar. 18, 2021

(65) Prior Publication Data

US 2022/0304171 A1    Sep. 22, 2022

(51) Int. Cl.
| | |
|---|---|
| *H05K 5/02* | (2006.01) |
| *F16M 11/10* | (2006.01) |
| *F16M 11/20* | (2006.01) |
| *F16M 13/02* | (2006.01) |
| *A61L 2/26* | (2006.01) |
| *A61L 2/10* | (2006.01) |
| *F16M 11/04* | (2006.01) |

(52) U.S. Cl.
CPC .............. *H05K 5/0204* (2013.01); *A61L 2/10* (2013.01); *A61L 2/26* (2013.01); *F16M 11/041* (2013.01); *F16M 11/10* (2013.01); *F16M 11/2021* (2013.01); *F16M 13/022* (2013.01); *A61L 2202/11* (2013.01)

(58) Field of Classification Search
CPC ........................... H05K 5/0204; F16M 11/041
See application file for complete search history.

(56) References Cited

U.S. PATENT DOCUMENTS

| | | | |
|---|---|---|---|
| 2019/0258300 A1* | 8/2019 | Gerardi ................. | G06F 1/1654 |
| 2020/0301480 A1* | 9/2020 | Miller ................... | E05D 11/082 |
| 2021/0278881 A1* | 9/2021 | Atom .................... | G06F 3/0202 |
| 2022/0091640 A1* | 3/2022 | Vassberg ............... | G06F 1/1626 |

* cited by examiner

*Primary Examiner* — Sherman Ng
(74) *Attorney, Agent, or Firm* — Leong C. Lei

(57) ABSTRACT

A quickly-fixable electronic device includes a fixing portion, a first base portion, and a second base portion. The fixing portion is provided with an electronic device. The first base portion is pivotally connectable with the fixing portion. The first base portion is provided with a receptacle. The receptacle receives and connects with the fixing portion. The second base portion is pivotally connected with the first base portion. The second base portion is provided with a magnetic attraction piece. The magnetic attraction piece enables quick fixing of the electronic device to a display screen. A pivoting motion between the fixing portion and the first base portion enables rotation of the electronic device by an angle. A pivoting motion between the first base portion and the second base portion enables inclining and swinging of the electronic device.

4 Claims, 6 Drawing Sheets

QUICKLY-FIXABLE ELECTRONIC DEVICE

TECHNICAL FIELD OF THE INVENTION

The present invention relates to an electronic device, and more particularly to an electronic device that includes a fixing structure.

DESCRIPTION OF THE PRIOR ART

In the modern world, there are a variety of electronic devices available I the market, such as mobile phones, tablet computers, electronic books, electronic lamps, cameras, and projectors. Such electronic devices may include a built-in fixing structure or is fixable by means of an external assisting fixing structure to a screen, a wall, or other fixed surfaces.

Taiwan Utility Model M387465 discloses an electronic device clamping and fixing device, which comprises a base, a cover, and an elastic unit and is formed of a combination of an upper portion including the cover and a lower portion including the base. The base and the cover are connected in a pivoting manner. The elastic unit causes the cover and the base to pinch in a direction toward each other. On the opposing surfaces of the base and the cover, the base is provided with a positioning piece, while the cover is provided with a retaining piece. In use, an electronic device is set such that a top and a bottom of the electronic device are respectively set in contact with the retaining piece and the positioning piece, while the elastic unit provides an acting force for the base and the cover to pinch and clamp the electronic device, and electronic device is thus fixed in the clamping and fixing device in a manner of being set at an angle. For a commonly available electronic product (electronic device), external assisting fixing structures that are known can be used to fix the electronic product (electronic device), but is not rotatable or has only a very limited range of rotation. In case that the electronic device is a mobile phone or a tablet computer, then the electronic device can only be viewable from a fixed direction. In case that the electronic device is an electronic lamp, then the electronic device can only irradiate a fixed direction, causing undesired limitation to the rotation angle and range. Further, the prior art devices do not allow for quick fixing of the electronic device to a display screen, a wall, or other fixed surfaces.

SUMMARY OF THE INVENTION

To overcome the above problem, the present invention provides a quickly-fixable electronic device, which comprises: a fixing portion, a first base portion, and a second base portion. The fixing portion is provided with an electronic device. The first base portion is pivotally connectable with the fixing portion. The first base portion is provided with a receptacle. The receptacle receives and connects with the fixing portion. The second base portion is pivotally connected to the first base portion. The second base portion is provided with a magnetic attraction piece, and the magnetic attraction piece is attachable, through attraction, to a display screen.

Preferably, a first pivot axle is provided between the fixing portion and the first base portion.

Preferably, a second pivot axle is provided between the first base portion and the second base portion.

Preferably, the fixing portion comprises a fixing portion body and a connection protrusion; and the fixing portion body is connected with the electronic device, and the connection protrusion is receivable in and connectable with the receptacle of the first base portion.

Preferably, the second base portion is provided, at one side thereof, with a positioning member.

The present invention makes use of the magnetic attraction piece to quickly attach and fix the electronic device to a display screen, and further makes use of a pivoting motion between the fixing portion and the first base portion to enable rotation of the electronic device by an angle, and further makes use of a pivoting motion between the first base portion and the second base portion to enable inclining and swinging of the electronic device. For example, the electronic device, in an example of being an ultraviolet germicidal lamp, may be first rotated by an angle to then irradiate at an inclined condition so as to expand the range of irradiation. Further, the fixing portion is removable out of the receptacle for replacement or exchange of the electronic device.

DETAILED DESCRIPTION OF THE PREFERRED EMBODIMENT

Figure 1:
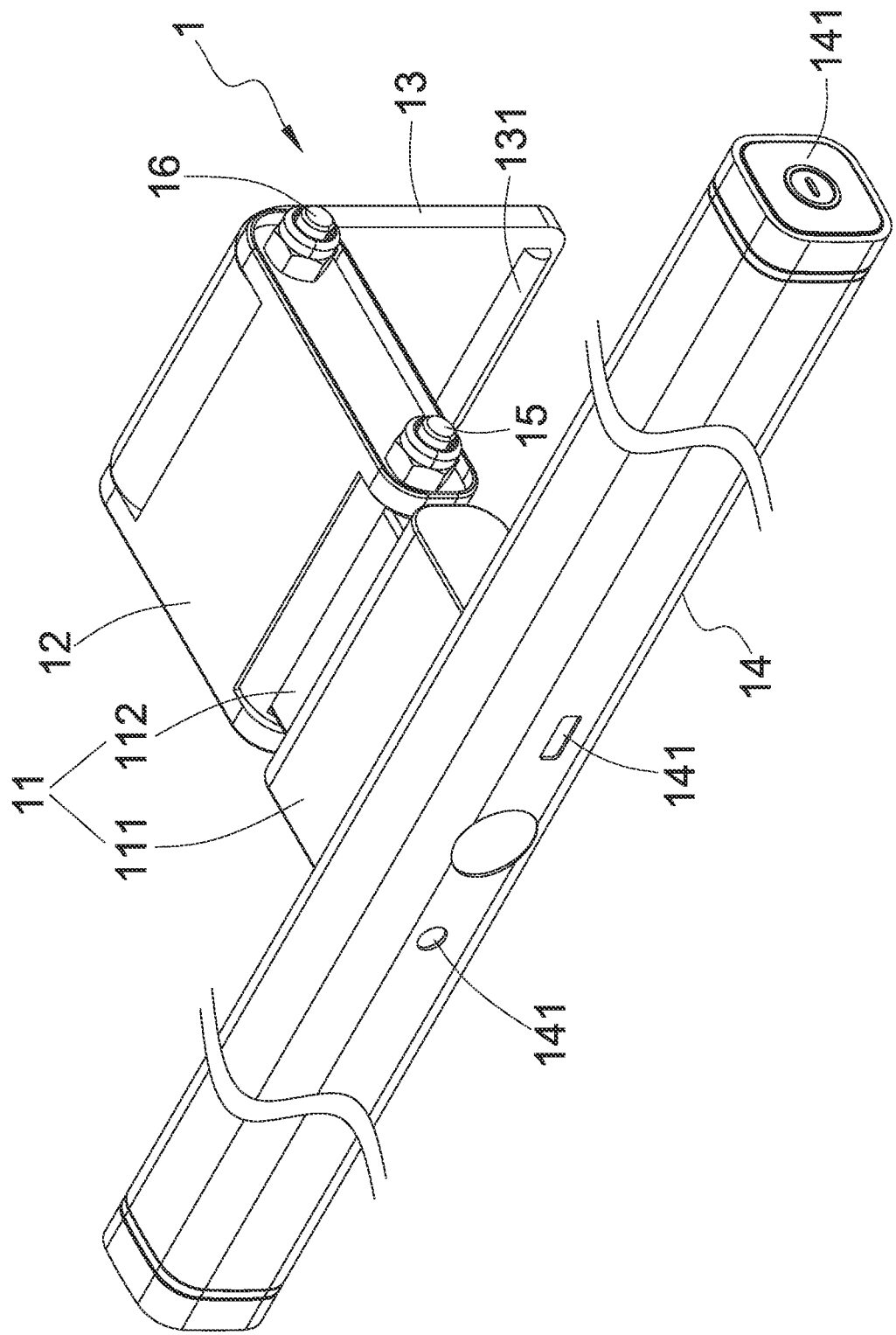
FIG. 1 is a perspective view showing a quickly-fixable electronic device according to the present invention.

Referring to FIG. 1, the present invention provides a quickly-fixable electronic device 1, which comprises: a fixing portion 11, a first base portion 12, and a second base portion 13.

The fixing portion 11 includes or is combined with, in any known means, an electronic device 14. The electronic device 14 can be an electronic lamp, a camera, or a projector. The electronic device 14 is provided with at least one function button 141. An example includes an ultraviolet germicidal lamp, and the ultraviolet germicidal lamp may include an automatic brightness regulation button, a switch button, and a data input port. This is known technology and is not a novel part of the present invention, so that further details are omitted herein.

Figure 2:
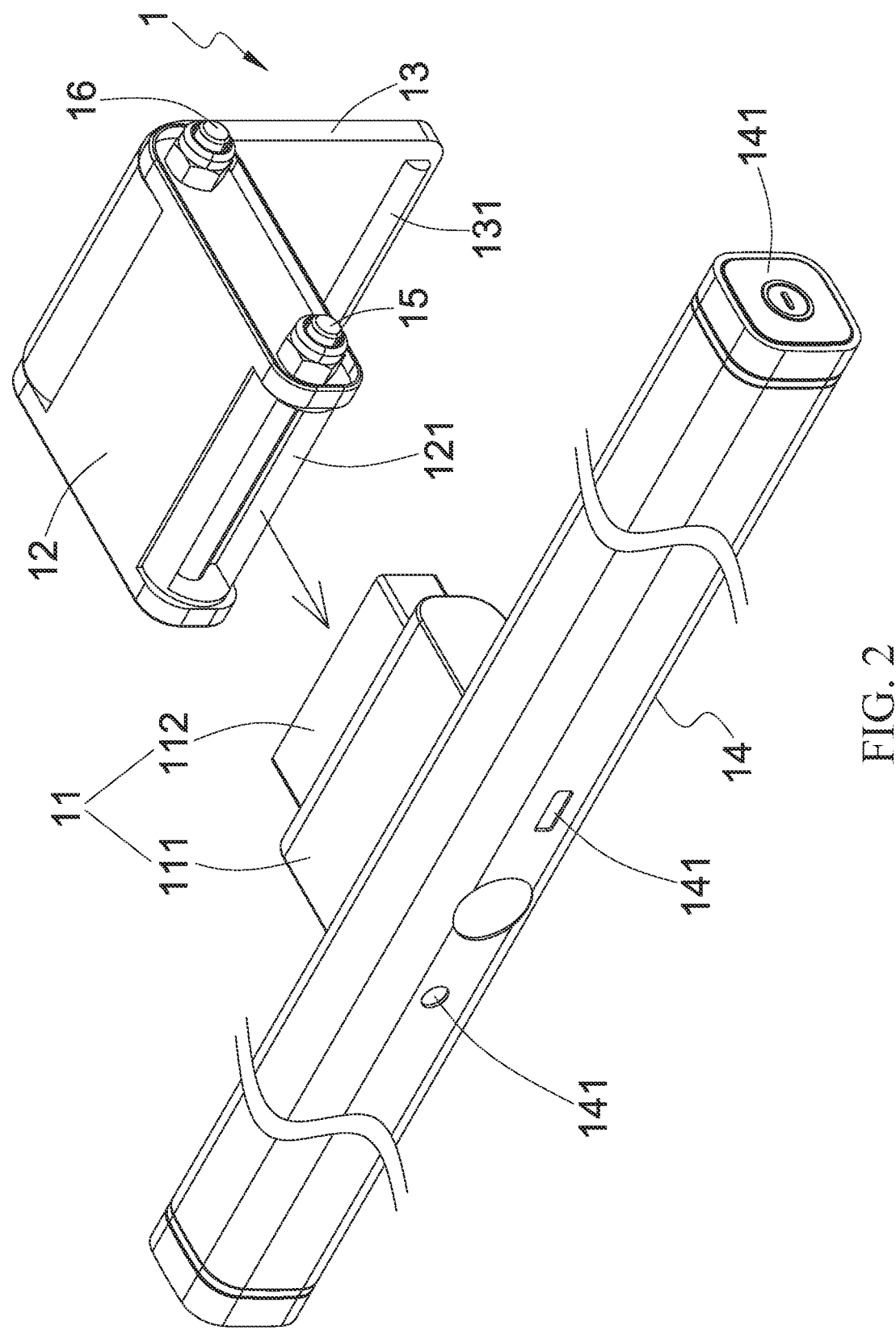
FIG. 2 is a perspective view showing a fixing portion being removed out of a receptacle provided in a first base portion.

Referring to FIG. 2, a first pivot axle 15 is provided between the fixing portion 11 and the first base portion 12, such that the first base portion 12 and the fixing portion 11 are pivotally connected. The first base portion 12 is formed with a receptacle 121. The receptacle 121 receives the fixing portion 11 to set therein and attach thereto. The fixing portion 11 is provided, at one side thereof, with a power input port for connection with a power cable. As such, the electronic device 14 can be attached to and combined with the receptacle 121 provided in the first base portion 12 through inward inserting and outward pulling. In a specific embodiment, the fixing portion 11 comprises a fixing portion body 111 and a connection protrusion 112. The fixing portion body 111 is connected with the electronic device 14, and the connection protrusion 112 is received in and attached to the receptacle 121 provided in the first base portion 12. Generally, the connection protrusion 112 has a size that is smaller than the fixing portion body 111, and the receptacle 121 includes a receiving space that is large enough to receive and accommodate the connection protrusion 112 therein.

Figure 6:
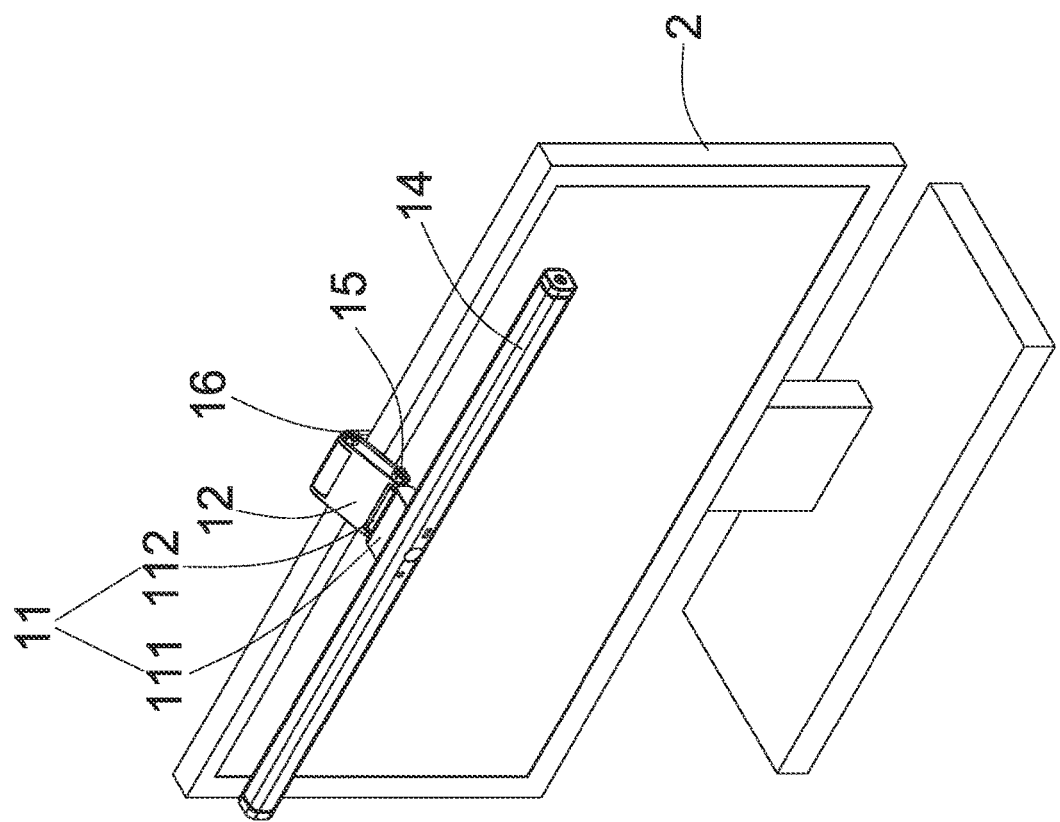
FIG. 6 is a schematic view illustrating the electronic device is fixed to a display screen.

A second pivot axle 16 is provided between the first base portion 12 and the second base portion 13, such that the second base portion 13 and the first base portion 12 are pivotally connected. The second base portion 13 is provided with a magnetic attraction piece 131. The magnetic attraction piece 131 may be or may include a magnet or a magnetic substance, of which a preferred example is a powerful permanent magnet. The magnetic attraction piece 131 may be attached, through magnetic attraction, to a display screen 2 (see FIG. 6). The display screen 2 is provided with an iron the ferrous plate corresponding to the magnetic attraction piece 131 to receive the magnetic attraction piece 131 to attach thereto. The display screen 2 can be a liquid crystal display (LCD) based display screen, an organic light-emitting diode (OLED) based display screen, or a display screen of other types.

Figure 3:
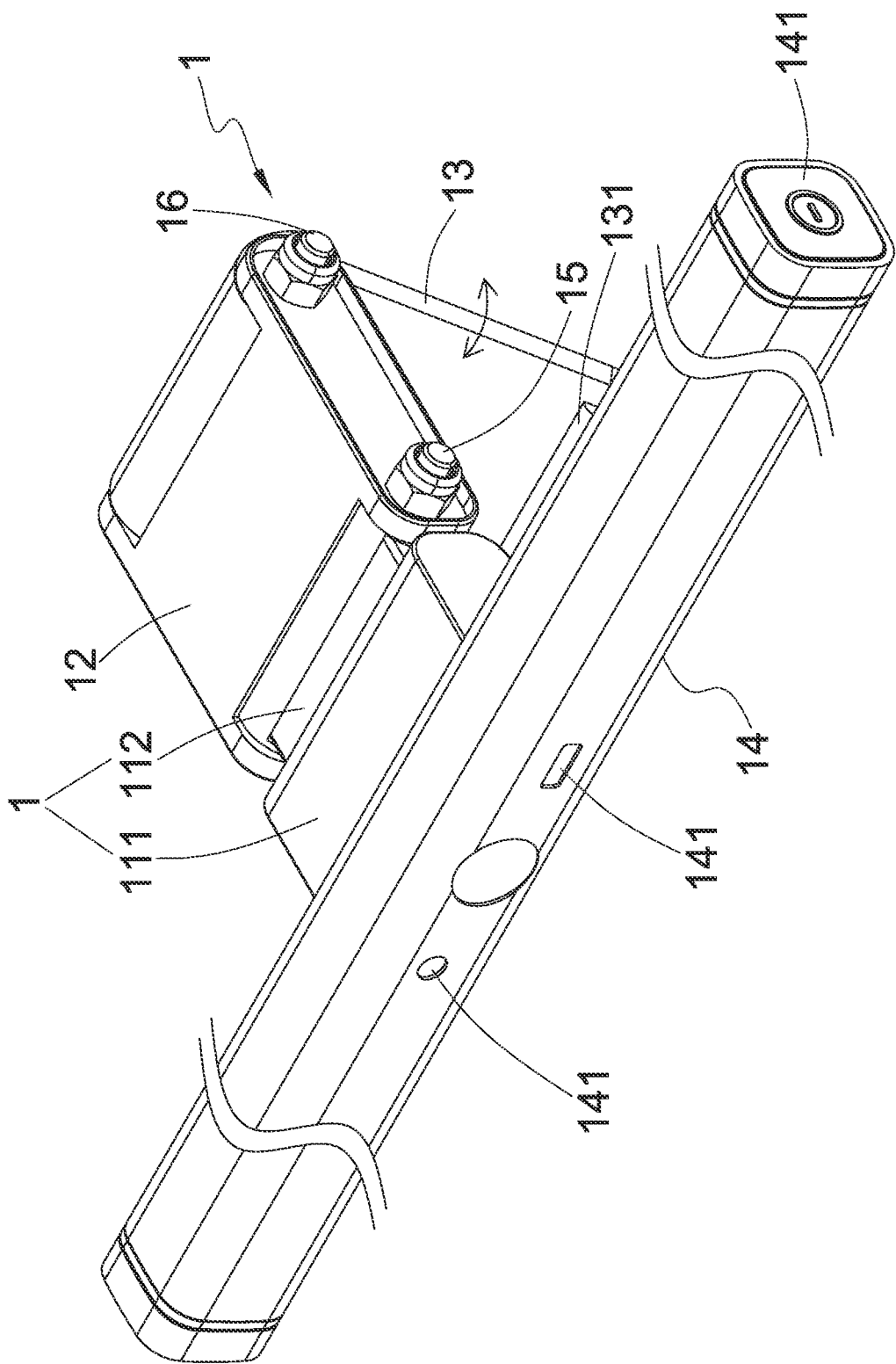
FIG. 3 is a first schematic view illustrating an operation of rotating of the quickly-fixable electronic device according to the present invention.
Figure 4:
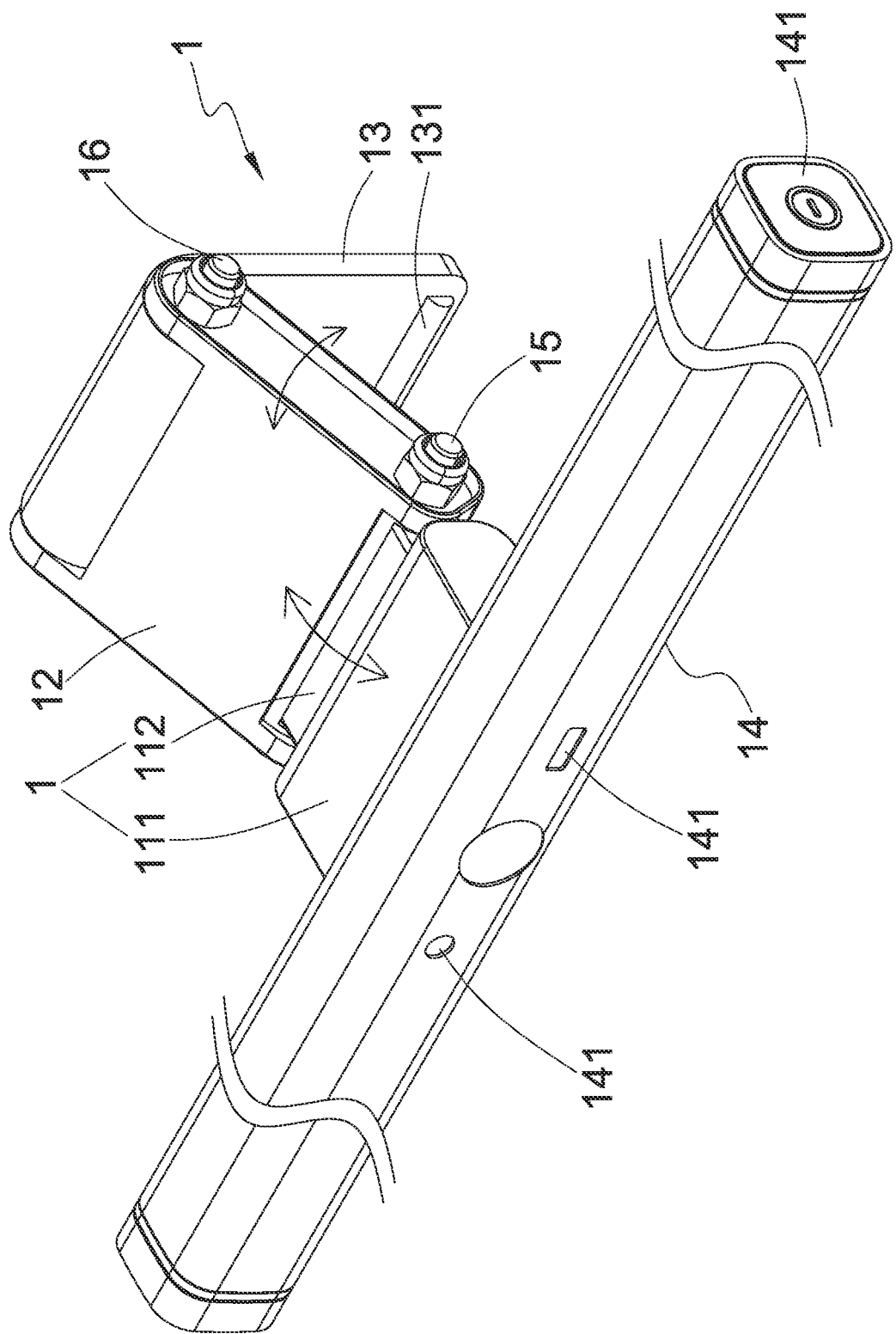
FIG. 4 is a second schematic view illustrating an operation of rotating of the quickly-fixable electronic device according to the present invention.

Referring to FIGS. 3 and 4, the present invention makes use of the magnetic attraction piece 131 to quickly attach and fix the electronic device 14 to the display screen 2 (see FIG. 6), and further make use of a pivoting motion of the first pivot axle 15 between the fixing portion 11 and the first base portion 12 to enable rotation of the electronic device 14 for a desired angle, and further make use of a pivoting motion of the second pivot axle 16 between the first base portion 12 and the second base portion 13 to inclining and swinging of the electronic device 14, so that a rotation range of the electronic device 14 is expanded and adjustment of angular position is made flexible with increased options for selection. For example, the electronic device 14, in an example of being an ultraviolet germicidal lamp, may be first rotated by an angle to then irradiate at an inclined condition so as to expand the range of irradiation. Further, the fixing portion 11 is removable out of the receptacle 121 of the first base portion 12 (as illustrated in FIG. 2) for replacement or exchange of the electronic device 14.

Figure 5:
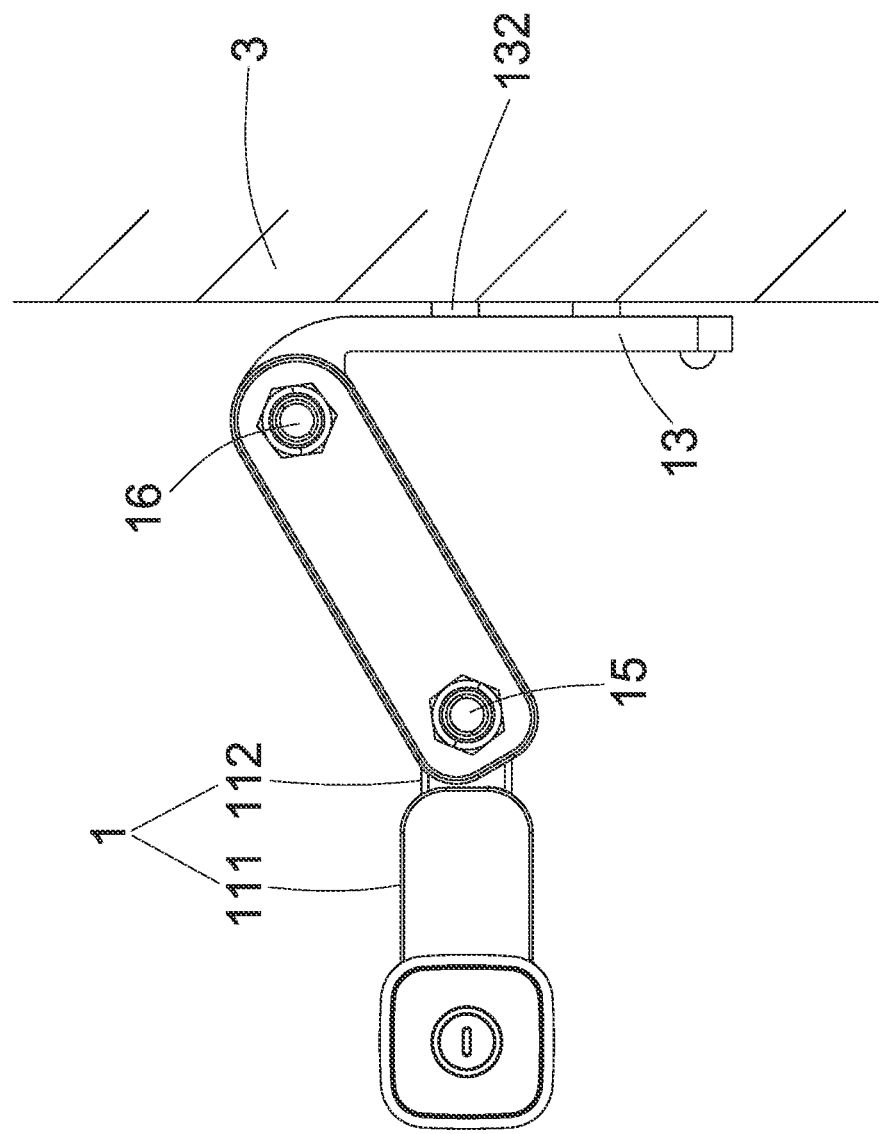
FIG. 5 is a schematic view illustrating the electronic device is fixed to a wall.

Referring to FIG. 5, the second base portion 13 may be provided, at one side thereof, with a positioning member 132. The positioning member 132 can be a hook, a suction cup, a clamp, a magnet, a hanger, a clip, or a buckle that is positionable to attach to a wall 3. The wall is provided with a counterpart member for achieving such positioning. For example, in case that the positioning member 132 is a magnet, the wall 3 is provided with a ferrous plate for magnetic attraction for attachment. Further, in case that the positioning member 132 is a buckle or clip, then the wall 3 is provided with a horizontal bar for clipping engagement.

I claim:

1. A quickly-fixable electronic device, comprising:
   a fixing portion, which is provided with an electronic device;
   a first base portion, which is pivotally connectable with the fixing portion, the first base portion being provided with a receptacle, the receptacle receiving and connecting with the fixing portion; and
   a second base portion, which is pivotally connected to the first base portion, the second base portion being provided with a magnetic attraction piece;
   wherein a first pivot axle is provided between the fixing portion and the first base portion.

2. The quickly-fixable electronic device according to claim 1, wherein a second pivot axle is provided between the first base portion and the second base portion.

3. The quickly-fixable electronic device according to claim 1, wherein the fixing portion comprises a fixing portion body and a connection protrusion, the fixing portion body being connected with the electronic device, the connection protrusion being receivable in and connectable with the receptacle of the first base portion.

4. The quickly-fixable electronic device according to claim 1, wherein the second base portion is provided, at one side thereof, with a positioning member.

* * * * *